(12) United States Patent
Stowell et al.

(10) Patent No.: US 6,284,163 B1
(45) Date of Patent: Sep. 4, 2001

(54) SOL-GEL ENCAPSULATION OF LIPID VESICLES, LIPID MEMBRANES AND PROTEINS

(75) Inventors: Michael H. B. Stowell, Cambridge (GB); Guangyang Wang, Pasadena; Sunney I. Chan, South Pasadena, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 08/788,632

(22) Filed: Jan. 24, 1997

Related U.S. Application Data

(60) Provisional application No. 60/010,677, filed on Jan. 26, 1996.

(51) Int. Cl.[7] .............................. A61K 9/50; A61K 9/127
(52) U.S. Cl. ........................ 264/4.1; 264/4.3; 264/4.32; 264/4.7
(58) Field of Search ............... 264/4.1, 4.3, 4.32, 264/4.7

(56) References Cited

U.S. PATENT DOCUMENTS

| | | | |
|---|---|---|---|
| 5,321,075 | * 6/1994 | Liles ....................................... | 524/837 |
| 5,364,633 | 11/1994 | Hill et al. ............................. | 424/450 |

FOREIGN PATENT DOCUMENTS

| | | |
|---|---|---|
| 297164 | * 1/1992 | (DE) . |
| 2642305 | * 3/1990 | (FR) . |
| 2 642 305 | 8/1990 | (FR) . |

OTHER PUBLICATIONS

Nakamura et al., translation of Nippon Kagaku Kaishi (10), p. 116, 1990.*
Salama et al., translation of DD 297 164, Aug. 1990.*
Nakamura et al., Nippon Kagaku Kaishi (10), p1166–70 1990.*
Ishiwatari, "Formation of Silicone Coated Vesicle by Sol–Gel Method. TEM Observation" Chem. Lett. 1996, Chem. Abstr., vol. 124, 1996, Columbus, OH, Abstract No. 124:97660.
Lin, "vesicle Formation in Electrolyte Solutions of New Cationic Siloxane Surfactant" J. Phys. Chem., Chem. Abstr., vol. 118, 1993, Columbus, OH, Abstract No. 118:176485.
Hansenne–Richoux, "Liposomal Hair Compositions Containing Lipids and Siloxanes", EP 526289 A1 1993 (French), Chem. Abstr., vol. 118, 1993, Columbus, OH, Abstract No. 118:154168.

\* cited by examiner

*Primary Examiner*—Jeffrey C. Mullis
(74) *Attorney, Agent, or Firm*—Fish & Richardson P.C.

(57) ABSTRACT

Inorganic-organic hybrid mixture sol-gel encapsulated lipid vesicles which are composed of silyl lipids or a mixture of silyl lipids and phospholipids are provided. The present invention also provides encapsulated Langmuir Blogget (LB) membranes and biological macromolecules. The sol-gel encapsulated lipid vesicles, LB membranes and proteins possess a higher stability than conventional vesicles. Inorganic-organic hybrid mixture sol-gels are provided as novel sol-gel materials possessing desirable mechanical and physicochemical properties. Also provided are methods of preparing encapsulated lipid vesicles, LB membranes and proteins. Methods of performing renal dialysis using compositions of the invention are also provided.

15 Claims, 7 Drawing Sheets

*View parallel to the membrane*

*View orthoganol to the membrane*

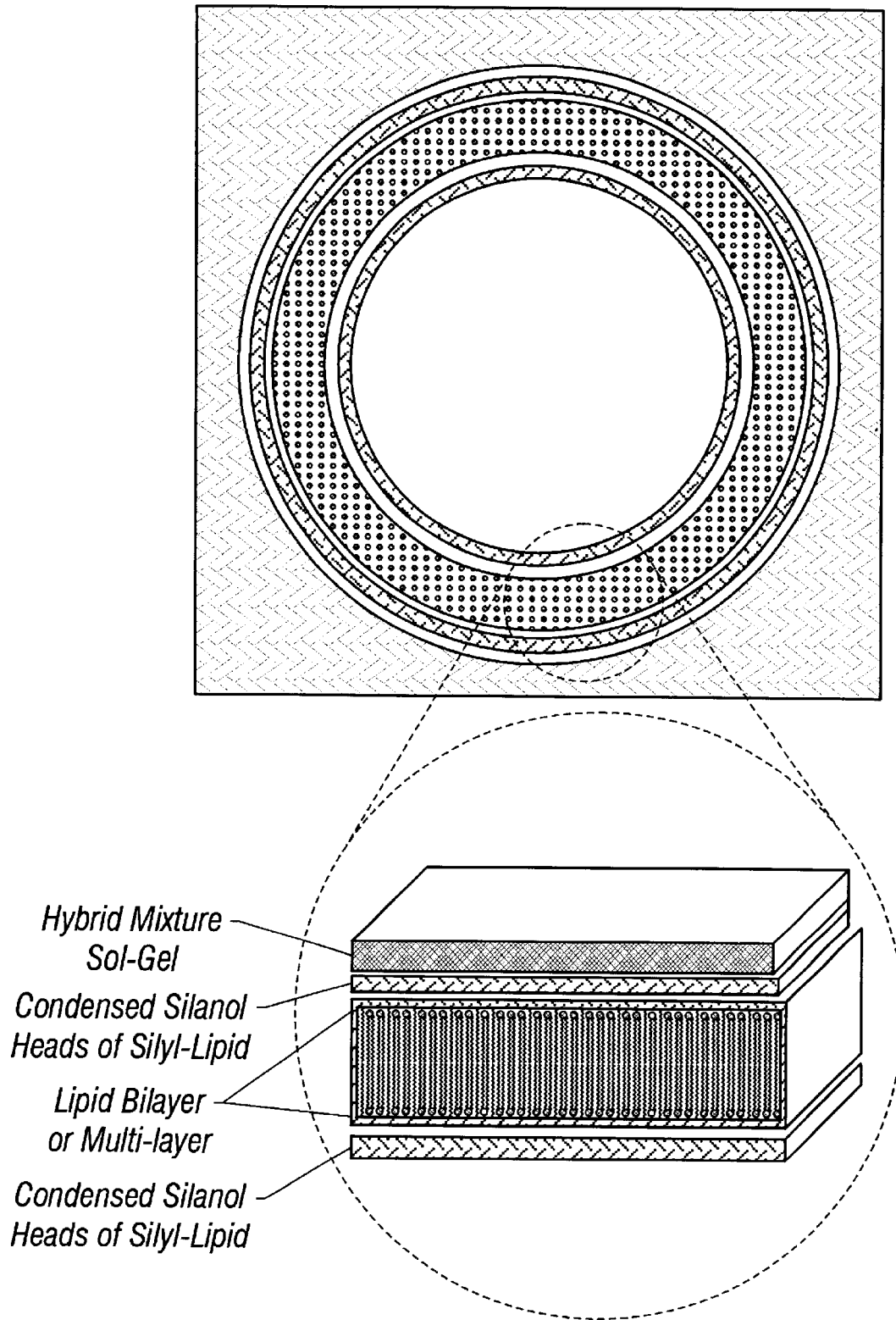
FIG._5

$(MeO)_3Si(CH_2)_2Si(OMe)_3$
$((EtO)_3SiCH_2CH_2CH_2)_2NH$
$(MeO)_3Si(CH_2)_3NH(CH_2)_2NH(CH_2)_3Si(OMe)_3$
$(MeO)_3Si(CH_2)_3NHCON(CH_2)_3Si(OMe)_3$
$(MeO)_3Si(CH_2)_3NHCOO(CH_2CH_2O)_nCONH(CH_2)_3Si(OMe)_3 \quad n=1,2,3,4$
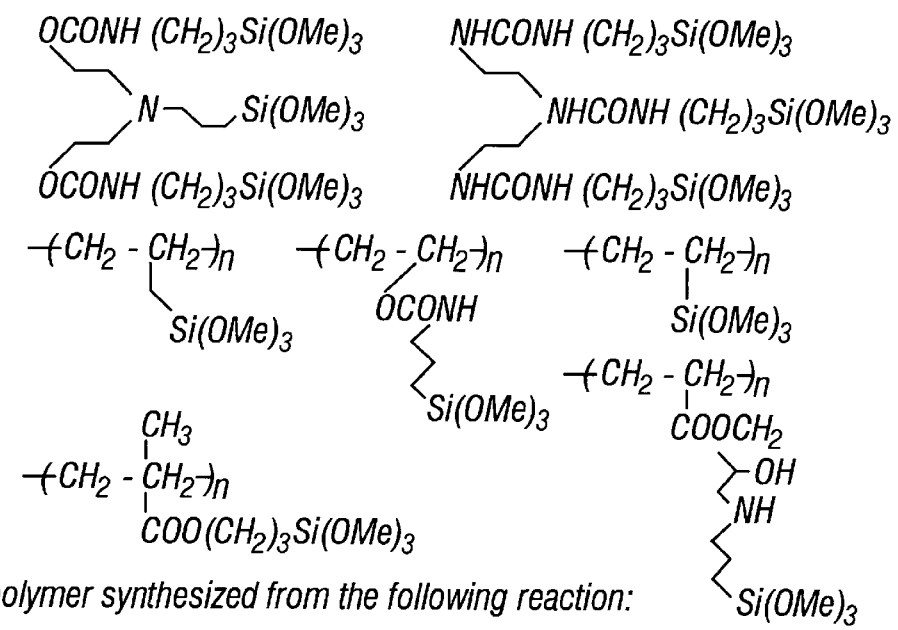
And polymer synthesized from the following reaction:
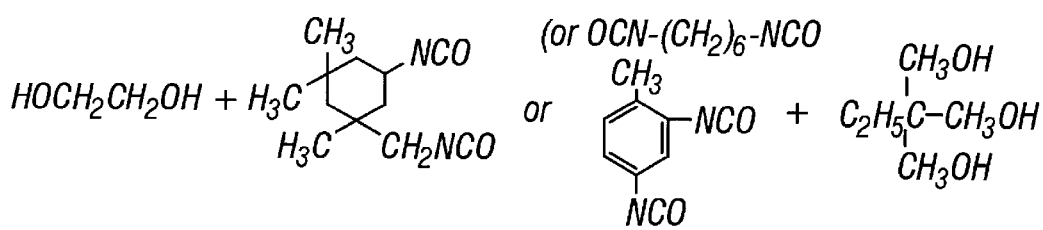
FIG. 7

SOL-GEL ENCAPSULATION OF LIPID VESICLES, LIPID MEMBRANES AND PROTEINS

This application claims priority from U.S. provisional application No. 60/010,677, filed Jan. 26, 1996.

FIELD OF THE INVENTION

The present invention describes a novel encapsulation system. More specifically, the invention describes inorganic-organic hybrid mixture sol-gel encapsulated phospholipid vesicles and methods of preparing them. The invention also describes encapsulated Langmuir Blogget (LB) lipid membranes and proteins.

BACKGROUND OF THE INVENTION

Biological macromolecules catalyze specific reactions in biological systems. This makes them desirable reagents with a host of applications. However, the large-scale commercial viability of biological macromolecules is limited by critical factors that include poor stability under and limited tolerance to industrial operational conditions, technical difficulties in recovery, and recycling from the reaction systems.

Lipid membranes and vesicles mimic the biological cell structure. Due to its self-assembled uniform structure and resultant physicochemical properties, they have gained more research attention and application in a variety of fields. However, lipid membranes and vesicles are fragile meta-stable systems. The monoleyer, bilayer and multilayer structures tend to be easily destroyed under varying conditions of temperature, external stress or changing media. Therefore, efforts are underway to immobilize biological macromolecules, lipid membranes and lipid vesicles in ways that stabilize and preserve their reactivity and uniform structure.

However, conventional sol-gel encapsulation procedures have limitations. The primary drawback is that the resultant gel is extremely fragile. It is easily broken under mechanical stress, so its encapsulation is not likely to provide a practical device. In spite of advances made in this area, there remains a need for a system that is endurable and whose mechanical properties may be modified as desired.

SUMMARY OF THE INVENTION

The present invention includes novel compositions comprising lipid vesicles or Langmuir-Blogget membranes (LB membranes) encapsulated with sol-gel encapsulation. The present invention also includes compositions comprising proteins entrapped in the silyl lipid membranes or vesicles which are encapsulated in sol-gel The lipid vesicles and LB membranes, which may be monolayer, bilayer or multilayer, are made from a variety of silyl lipids or their mixtures with phospholipids. The present invention also provides a sol-gel encapsulation composition comprising inorganic-organic hybrid mixture sol-gel. Hybrid mixture sol-gels possess enhanced mechanical properties. The present invention further provides methods for the preparation of sol-gel encapsulated compositions. The present invention also provides an application of the compositions of the invention in renal dialysis.

BRIEF DESCRIPTION OF THE DRAWINGS

FIG. 5 is a schematic showing a hybrid mixture sol-gel encapsulated vesicle.

FIG. 7 shows the precursor molecules used in the preparation of hybrid mixture sols.

DETAILED DESCRIPTION OF THE INVENTION

Figure 1:
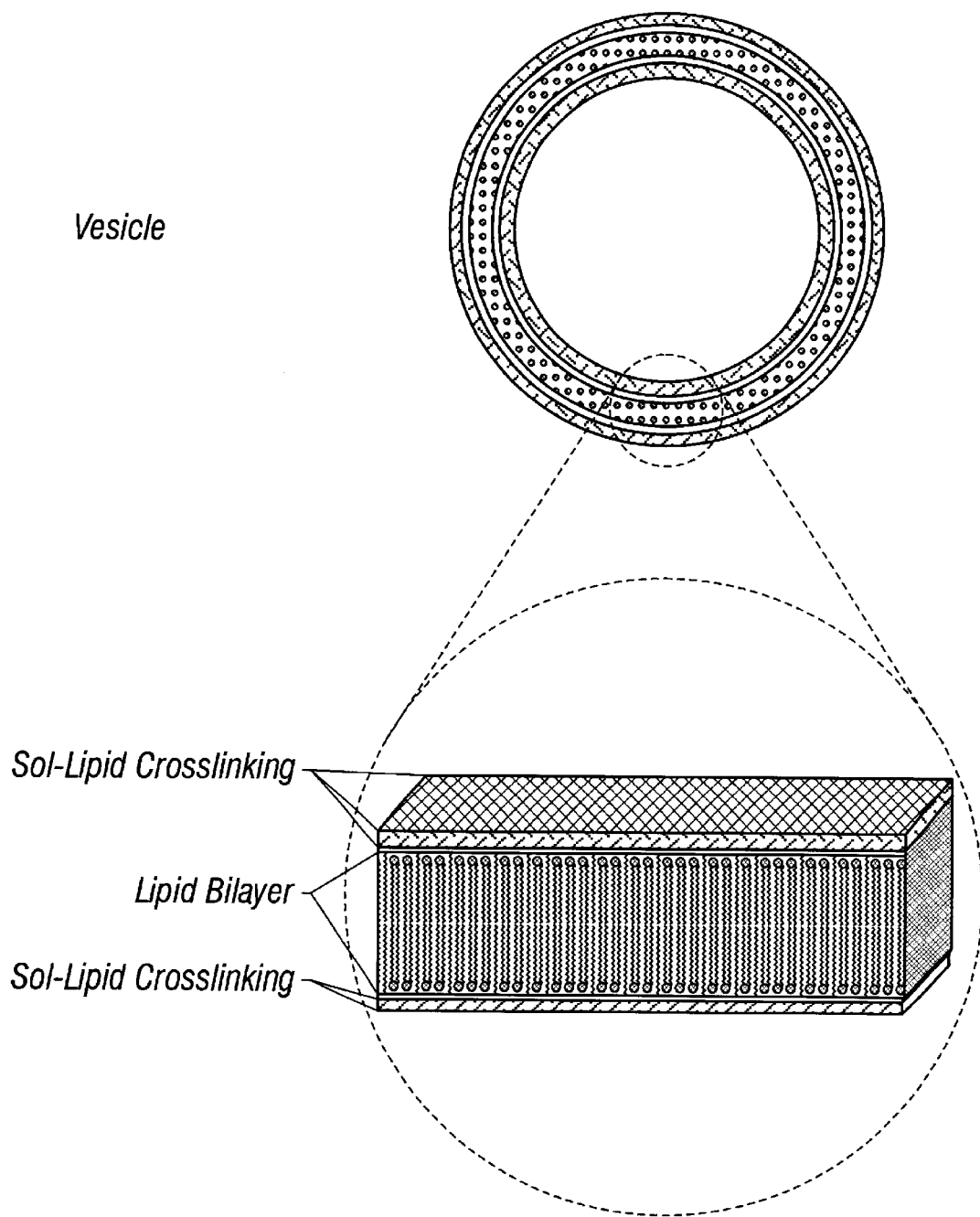
FIG. 1 is a schematic of a cross-linked sol-gel encapsulated phospholipid vesicle.
Figure 2A:
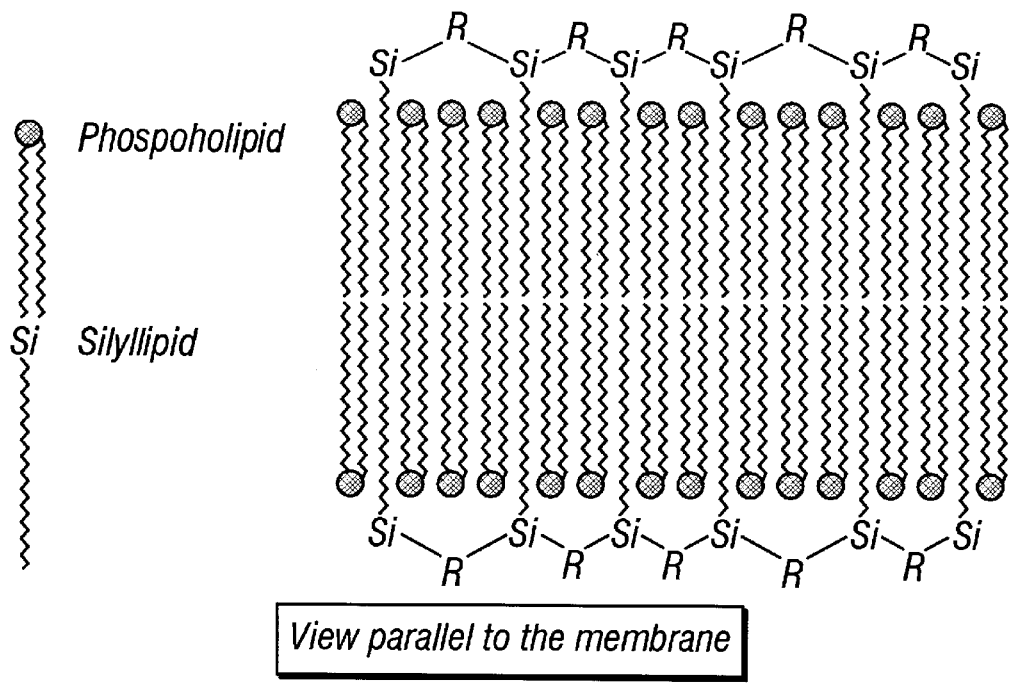
FIG. 2(a) is a schematic showing a parallel view of a cross-linked sol-gel encapsulated phospholipid vesicle.
Figure 2B:
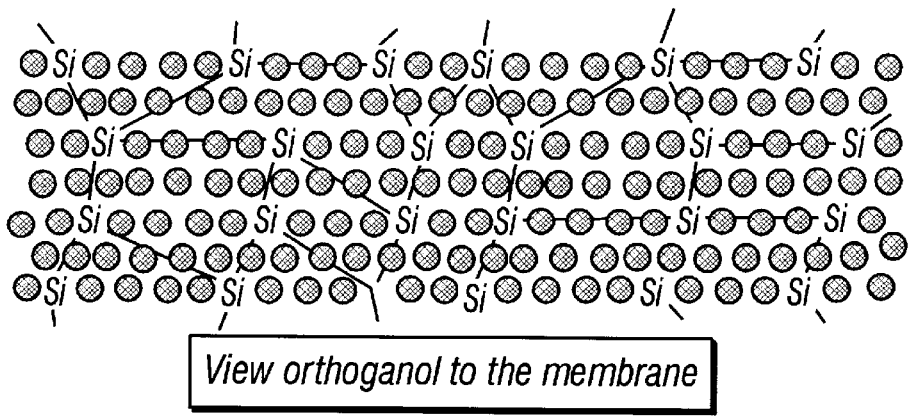
FIG. 2(b) is a schematic showing an orthogonal view of a cross-linked sol-gel encapsulated phospholipid vesicle.
Figure 3:
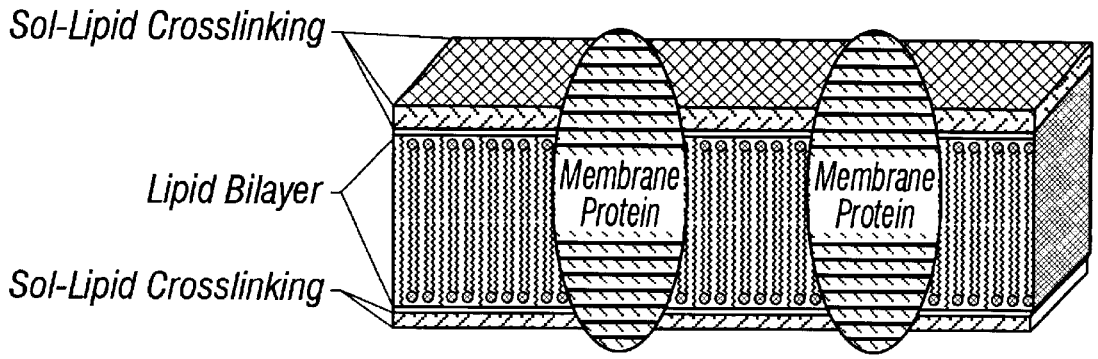
FIG. 3 is a schematic of a sol-gel encapsulated membrane protein entrapped in a surface cross-linked lipid bilayer (silyl lipid or its mixture with phospholipids).
Figure 4A:
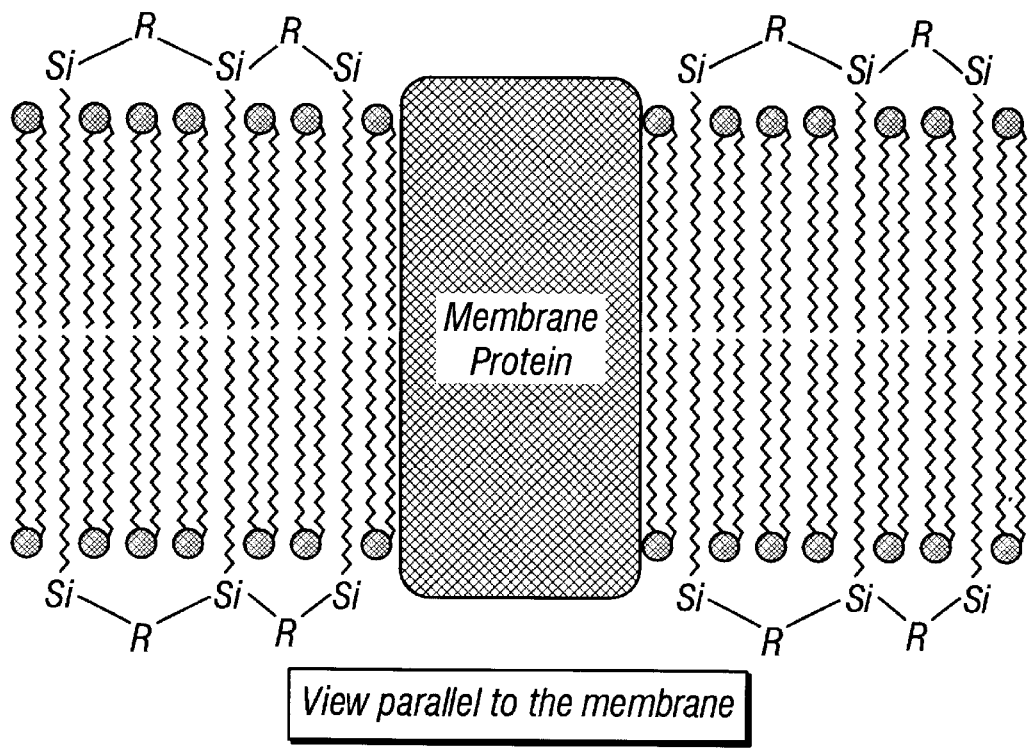
FIG. 4(a) is a schematic showing a parallel view of a cross-linked sol-gel encapsulated membrane protein (silyl lipid or its mixture with phospholipids).
Figure 4B:
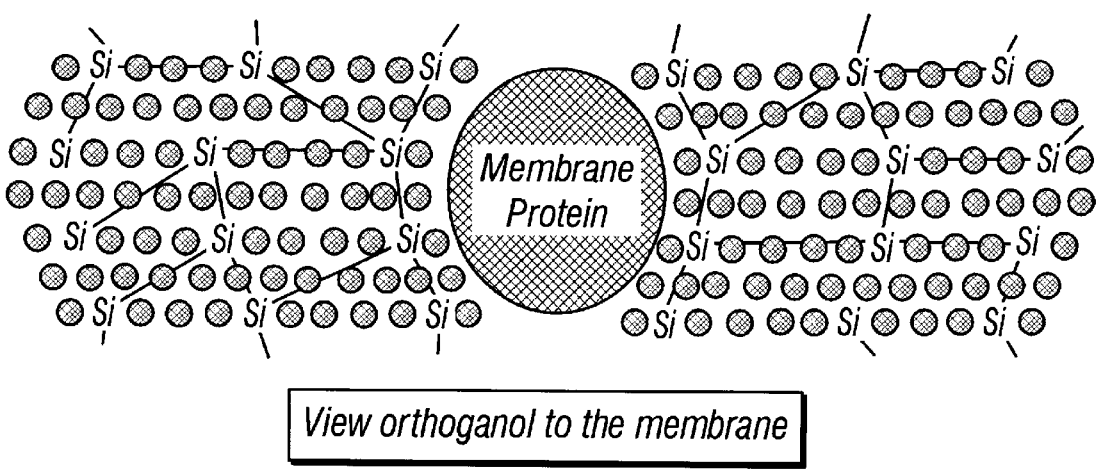
FIG. 4(b) is a schematic showing an orthogonal view of a sol-gel encapsulated membrane protein (silyl lipid or its mixture with phospholipids).
Figure 6A:
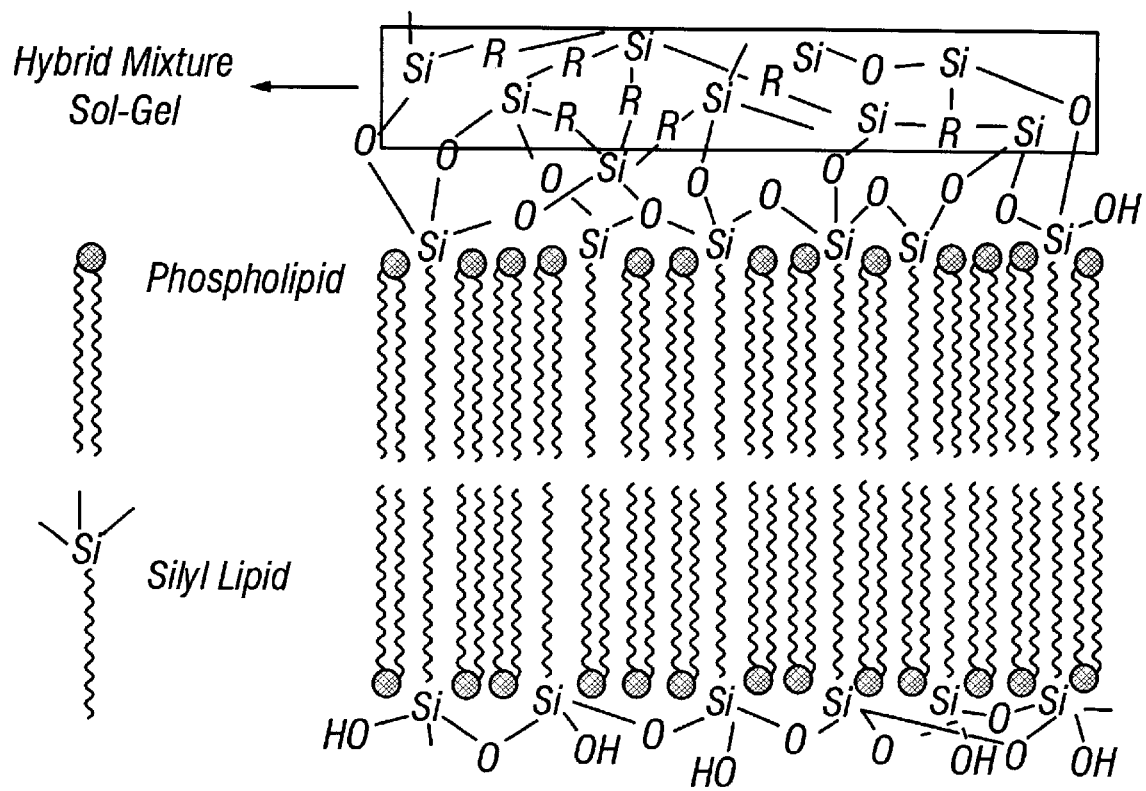
FIG. 6(a) is a schematic showing a parallel view of a hybrid mixture sol-gel encapsulated vesicle.
Figure 6B:
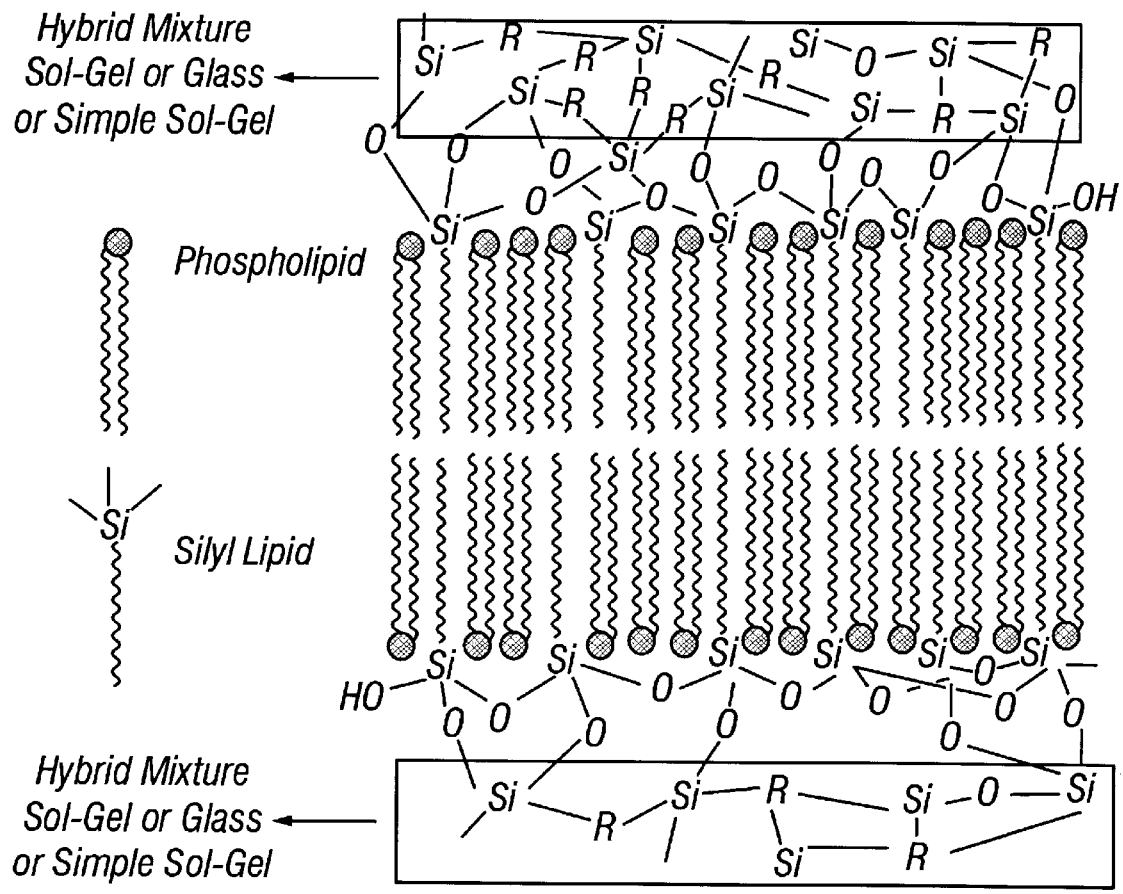
FIG. 6(b) is a schematic showing a view of a hybrid mixture sol-gel encapsulated vesicle parallel to the "sandwiched" LB membrane.

A colloidal solution or sol is the term used to denote liquid media containing solid particles. A colloidal sol that forms a gel is termed sol-gel. The present invention provides compositions comprising sol-gel encapsulated phospholipid vesicles. These compositions also include sol-gel encapsulated proteins. The compositions of the present invention comprise inorganic-organic hybrid mixture sol-gel encapsulated lipid bilayers or multilayers (which form the microstructure of lipid vesicles and LB membranes). These compositions are composed of silyl lipids or a mixture of silyl lipids and phospholipids. The silyl lipid refers to the lipid molecules that are attached with a silanol group at one end, thereby able to form a monolayer, bilayer or multilayer structure after hydrolysis. In the present invention, the silyl lipids are cross-linked via hydrolysis and condensation with the silanol groups or heads at the surface of the vesicles of LB membranes, and with the encapsulating hybrid mixture sol-gel matrix, to enhance stability of the vesicles and lipid membranes.

Further, the compositions of the invention may include encapsulated proteins. It is preferred that the membrane be entrapped in the lipid bilayer prior to encapsulation of the bilayer by a simple sol-gel or hybrid mixture sol-gel.

The compositions of the present invention are expected to have enhanced thermal and mechanical stability compared to conventional phospholipid vesicles and phospholipid LB membranes. Moreover, these compositions find application in ion specific filtration and desalination, and as detectors, biosensors, biocatalysts, high performance materials, optical and diagnostic devices.

The silyl lipids used in the compositions of the present invention, obtained after hydrolysis, are preferably of the formula:

wherein:
R is selected from a group consisting of $C_1$–$C_{50}$ alkyl;
R' is selected from a group consisting of $(CH_2)_qA$ and $OSiR_3$;
A is selected from a group consisting of hydrogen, $COO^-$, OH, COOH, $N^+R_1R_2R_3$, NHR", SH, SR" and $C_1$–$C_{50}$ alkyl;

$R_1$, $R_2$, $R_3$ and R" are selected from a group consisting of $(CH_2)_qCH_3$ and $(CH_2)_qSi(OR)_3$;

q is a number from 1 to 50;

n is a number from 1 to 4; and m is a number from zero to 3.

The silyl lipid functions not only as a component lipid molecule to form a bilayer or multilayer structure in the LB membrane or vesicle, but also as a cross-linking seed such that condensation of the silanol head with the silyl lipid results in the formation of a fine mesh at the surface of the lipid membrane or vesicle, thus enhancing the stability of the membrane or vesicle. Furthermore, silyl lipids may co-condense with the silanol groups at the surface of the encapsulating material or matrix (sol-gel, hybrid mixture sol-gel or glass), thus covalently bonding with the matrix and improving its stability.

Compositions of the present invention also include encapsulation by inorganic-organic hybrid mixture sol-gels. A monomeric or polymeric molecule bearing two or more silyl alkoxides and an organic linkage between the silyl alkoxide pendants is referred to as an inorganic-organic hybrid silyl molecule. A sol solution prepared by the co-hydrolysis of several different inorganic-organic hybrid silyl molecules with or without tetraalkoxy silanes is termed a hybrid mixture sol. A hybrid mixture sol-gel is obtained from a hybrid mixture sol by condensation with silanol groups. During condensation, the organic species are cross-linked together by siloxane bonds to form gels. The selection of hybrid precursors ensures that the length of the organic linkage between two silyl alkoxides in one molecule is different from that in the other molecules. This results in a gel having a combination of organic linkage lengths, thus having preferred mechanical properties ranging from fragile glass to quasi elastomers. A variety of hybrid silyl precursor molecules may be used in the compositions of the present invention (FIG. 7).

The present disclosure also provides methods for sol-gel encapsulation of lipid membranes (e.g. bilayers) to prepare "sandwiched" LB membranes. LB lipid membranes made from silyl lipid, or its mixture with phospholipids, is sandwiched between two layers of glass, sol-gel or hybrid mixture sol-gel. The silanol groups at the surface of the lipid membrane are condensed with each other and with the silanol groups at the surface of the glass, sol-gel or hybrid mixture sol-gel, thereby being covalently bonded to the encapsulating matrix. Compared to conventional lipid LB membranes, the encapsulated membrane possesses enhanced thermal and mechanical properties, and can be utilized in a variety of applications.

A variety of proteins may be introduced in the hybrid mixture sol-gel. The mechanical and optical properties of the hybrid mixture sol-gel facilitate practical industrial applications of proteins. A hybrid mixture sol-gel prepared from hybrid precursor silyl molecules, which bear hydrophilic groups along with the inherently hydrophilic silanol groups, facilitates preservation of the reactivity of proteins. For membrane proteins that require a hydrophobic environment, it is preferable to entrap the protein in a lipid membrane and then encapsulate the protein and lipid membrane with a sol-gel or hybrid mixture sol-gel, or sandwich between glass layers.

Preferred embodiments provide two classes of sol-gel encapsulated vesicles: Class I materials which are solution hybrid mixture sol-gel encapsulated vesicles; and Class II materials which are solution hybrid mixture sol-gel encapsulated vesicles. Class I vesicles are produced by mixing a hybrid mixture sol solution with a phospholipid vesicles solution, followed by condensation. Class II vesicles are made from silyl lipids or a mixture of silyl lipids and phospholipids. The silyl lipids form a mesh over the vesicles and bond the vesicles to the encapsulating hybrid mixture sol-gel matrix. In a preferred embodiment, the covalent siloxane cross-linkage extends over the surface of the lipid bilayer or multilayer in the form of a fine mesh. The mesh is also covalently bonded to the hybrid mixture sol-gel matrix via the same siloxane cross-linkage. Due to the increased stability of the sol-gel encapsulated vesicles of the present invention, they are less susceptible to rupture as compared to conventional phospholipid vesicles.

The sol-gel encapsulation of lipid vesicles, membranes and proteins in the present invention can also be applied to other metal alkoxides, including those of Ti, Zr and Bi.

Solution sol-gel encapsulation is achieved by mixing the sol or the monomer with a phospholipid vesicle solution, followed by polymerization.

Surface sol-gel encapsulation involves the use of silyl lipid molecules which crosslink to form a mesh over the phospholipid vesicles, thereby encapsulating the vesicles.

The following examples illustrate the invention and are not intended to limit the same.

EXAMPLES

Phospholipids are obtained from Avanti Polar Lipids, Inc. (Birmingham, Ala.). Silyl-lipids are obtained from United Chemical Technologies (Bristol, Pa.). All other chemicals are of standard reagent grade.

Example 1

Preparation of Phospholidid Vesicles

A phospholipid such as egg phosphatidylcholine (20 mg) was dissolved in double distilled water (1 mL) with sonication to form large multilamellar vesicles. The resulting vesicle solution was frozen using liquid nitrogen and thawed in a water bath at 60° C. for five freeze-thaw cycles. Following that, the multilamellar vesicles were filtered by passing through a 100 nm polycarbonate or inorganic alumina filter. The filtering process may be repeated as many times as necessary. Filtration resulted in the formation of small unilamellar vesicles (SUV). A variety of phospholipids may be used for the formation of vesicles such that optimal loading and short time stability may be achieved.

Example 2

Preparation of Inorcanic-organic Hybrid Mixture Sol

A mixture of the desired precursor hybrid molecules was dissolved in water (4–100 molar equivalents of alkoxy silanes in the hybrid precursor mixture) containing a catalytic amount of acid (such as hydrochloric acid) by sonication or vigorous stirring at 0° C. until homogenous.

Example 3

Preparation of Sol-gel Encapsulated Phospholipid Vesicles

A solution of small unilamellar vesicles prepared from soya lecithin (according to Example 1) was mixed thoroughly with the hybrid mixture sol solution prepared according to Example 2, with stirring. The solution was then allowed to cure for about 2 to 15 days, after which the water was removed and the resulting gel air dried.

Example 4
Preparation of Sol-gel Encapsulated Vesicles Consisting Solely of Silyl Lipids or a Mixture of Silyl Lipids and Phospholilids A 0.1–1% acidic solution (pH less than 6) of n-octadecyldimethyl-(3-trimethoxysilylpropyl)ammonium chloride (or its mixture with soya lecithin) was sonicated for 5 minutes at 0° C. to form large multilamellar vesicles. The vesicle solution was then filtered by passing through a 100 nm polycarbonate syringe filter as many times as necessary to form small unilamellar vesicles (SUV). The resulting SUV solution was mixed thoroughly with pre-formed inorganic-organic hybrid mixture sol solution. The solution was allowed to cure for about 2 days to 4 weeks. A buffer of pH 6–7 may be added to speed gel formation and aging. The water was then removed and the gel air dried. A variety of phospholipids and silyl lipids may be used in the preparation of encapsulated vesicles such that there are variations in the chain length and head group functionality.

Example 5
Preparation of Sol-gel Encapsulated Soluble Proteins

Chloroperoxidase was dissolved in a phosphate buffer of pH 6.5. The solution was then thoroughly mixed with a pre-formed hybrid mixture sol solution, allowed to cure for about 2–4 weeks and then air dried for another 2–4 weeks.

Example 6
Preparation of Sandwiched LB Lipid Membranes (a) Preparation of the substrate: Three types of substrates have been used to prepare sandwiched LB lipid membranes. These include flat glass, flat sol-gel plates made from the hydrolysis and condensation of tetraalkoxy silane, and flat sol-gel plates made from inorganic-organic hybrid mixture sol. The glass surface was processed and cleaned to ensure the presence of a sufficient number of silanol groups at the glass surface free of contamination. The 2 types of sol-gel plates were prepared by the same method and equipment used in the preparation of mini-electrophoresis gel. After the gel was formed, it was allowed to cure for about 2 days to 4 weeks. After that, water was removed and the gel was air dried. Drying may also be carried out at 60–150° C. to speed up the drying process. The resulting sol-gel plate is flat and transparent, with a thickness of 0.5–5 mm.

(b) Preparation of sandwich LB membrane: n-Octadecyldimethyl-(3-trimethoxysilylpropyl) ammonium chloride (0.1–1%), or its mixture with soya lecithin, was dissolved in acidified distilled water (pH less than 6), with sonication. The solution was then transferred to a Langmuir minitrough (KSV Instruments Ltd., Finland) and compressed. The substrate was then repeatedly immersed into the minitrough. The LB membrane forms at the surface of the substrate. The substrate bearing the LB membrane was then immersed in a buffer solution (pH 6–7) and cured for 2–10 days at 0° C. After that, the membrane was immersed into a pre-formed hybrid mixture sol or uniform sol solution to sandwich the lipid bilayer or multilayer membrane. It was next immersed in a buffer solution (pH 6–7) and cured for another 2–15 days. The water was then removed and the membrane air dried.

Example 7
Sol-gel Encapsulation of Membrane Proteins

In Example 6(b), lipase or bacterial rhodopsin may be added to the vesicle solution after sonication. The procedure of Example 6 is then followed to acquire protein entrapped in the sandwiched lipid membrane.

Example 8
Use of Sol-gel Encapsulated Phospholipid Vesicles in Renal Dialysis Patients with renal failure develop acid/base imbalance in the blood stream and, therefore, require regular dialysis to maintain the appropriate blood pH. Current methods for dialysis employ systems wherein ammonia is transported across a dialysis membrane and is trapped by an acidic compound such as citric acid. Disadvantages of currently used dialysis membranes include short shelf life and instability during usage. The sol-gel encapsulated phospholipid vesicles of the present invention may be used in dialysis membranes, thus affording a more stable and efficient dialysis system than the currently used citric acid-based membrane. Ammonia exchange was quantitated by passing a solution of ammonium phosphate through the sol-gel encapsulated vesicle membrane and determining the output pH value.

What is claimed is:

1. A lipid vesicle composition comprising:

a plurality of silyl lipid molecules wherein said silyl lipid molecules further comprise at least one silanol group; wherein the at least one silanol groups of said plurality of silyl lipid molecules are joined together via siloxane bonds, wherein said silyl lipid is of the formula:

$(RO)_n SiR'_m$ wherein:

R is selected from a group consisting of $C_1$–$C_{50}$, alkyl;

R' is selected from a group consisting of $(CH_2)_q A$ and $OSiR_3$;

A is selected from a group consisting of hydrogen, $COO^-$, OH, COOH, $N^+R_1R_2R_3$, NHR", SH, SR" and $C_1$–$C_{50}$ alkyl;

$R_1$, $R_2$, $R_3$ and R" are selected from a group consisting of $(CH_2)_q CH_3$ and $(CH_2)_q Si(OR)_3$;

q is a number from 1 to 50;

n is a number from 1 to 4; and m is a number from zero to 3.

2. A lipid vesicle composition comprising:

a plurality of silyl lipid molecules wherein said silyl lipid molecules further comprise at least one silanol group; wherein the at least one silanol groups of said plurality of silyl lipid molecules are Joined together via siloxane bonds, which is encapsulated by an inorganic-organic hybrid mixture sol-gel or uniform sol-gel, further comprising phospholipid vesicles.

3. The composition of claim 2 wherein said inorganic-organic hybrid mixture sol-gel is a gel formed from an inorganic-organic hybrid mixture sol solution.

4. A Langmuir lipid membrane composition comprising:

a plurality of silyl lipid molecules wherein said silyl lipid molecules further comprise at least one silanol group; wherein the silanol groups are joined together via siloxane bonds, wherein said silyl-lipid is of the formula:

$(RO)_n SiR'_m$ wherein:

R is selected from a group consisting of $C_1$–$C_{50}$ alkyl;

R' is selected from a group consisting of $(CH_2)_q A$ and $OSiR_3$;

A is selected from a group consisting of hydrogen, COO⁻, OH, COOH, N⁺R₁R₂R₃, NHR″, SH, SR″ and $C_1$–$C_{50}$ alkyl;

$R_1$, $R_2$, $R_3$ and R″ are selected from a group consisting of $(CH_2)_qCH_3$ and $(CH_2)_qSi(OR)_3$;

q is a number from 1 to 50;

n is a number from 1 to 4; and m is a number from zero to 3.

5. A composition comprising:

an upper layer of encapsulation material, a lipid monolayer, bilayer or multilayer membrane, and a lower layer of supporting substrate or encapsulation material, said membrane having the composition of a Langmuir lipid membrane composition comprising:

a plurality of silyl lipid molecules wherein said silyl lipid molecules further comprise at least one silanol group; wherein the silanol groups are joined together via siloxane bonds, and being positioned between said upper layer of encapsulation material and said lower layer of supporting substrate or encapsulation material.

6. The composition of claim 5 wherein said encapsulating material is a uniform sol-gel or an inorganic-organic hybrid mixture sol-gel.

7. The composition of claim 6 wherein said hybrid mixture sol-gel is prepared from precursor molecules selected from the group consisting of:

$(MeO)_3Si(CH_2)_2Si(OMe)_3$,
$((EtO)_3SiCH_2CH_2CH_2)_2NH$,
$(MeO)_3Si(CH_2)_3NH(CH_2)_2NH(CH_2)_3Si(OMe)_3$,
$(MeO)_3Si(CH_2)_3NHCON((CH_2)_3Si(OMe)_3$,
$(MeO)_3Si(CH_2)_3NHCOO(CH_2CH_2O)_nCONH(CH_2)_3Si(OMe)_3$,

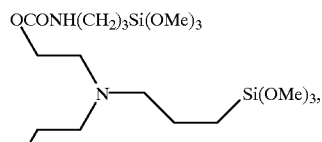

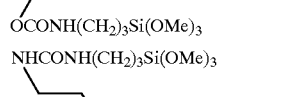

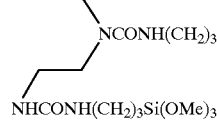

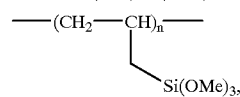 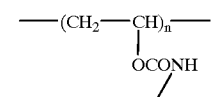

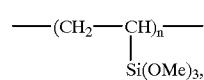 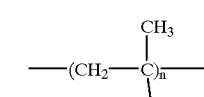

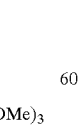

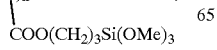

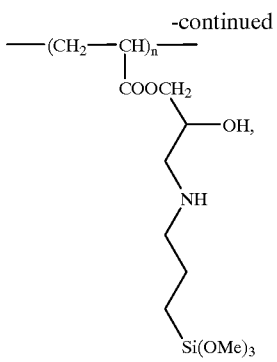

and combinations thereof where n = 1, 2, 3, or 4.

8. A composition comprising:

an upper layer of encapsulation material, a lipid bilayer or multilayer membrane, at least one biological macromolecule which is entrapped in said membrane, and a lower layer of supporting substrate or encapsulation material; said membrane having the composition of a Langmuir lipid membrane composition comprising:

a plurality of silyl lipid molecules wherein said silyl lipid molecules further comprise at least one silanol group; wherein the silanol groups are joined together via siloxane bonds, and being positioned between said upper layer of encapsulation material and said lower layer of supporting substrate or encapsulation material.

9. The composition of claim 8 wherein said encapsulating material is a uniform sol-gel or an inorganic-organic hybrid mixture sol-gel.

10. The composition of claim 9 wherein said hybrid mixture sol-gel is prepared from precursor molecules selected from the group consisting of:

$(MeO)_3Si(CH_2)_2Si(OMe)_3$,
$((EtO)_3SiCH_2CH_2CH_2)_2NH$,
$(MeO)_3Si(CH_2)_3NH(CH_2)_2NH(CH_2)_3Si(OMe)_3$,
$(MeO)_3Si(CH_2)_3NHCON((CH_2)_3Si(OMe)_3$,
$(MeO)_3Si(CH_2)_3NHCOO(CH_2CH_2O)_nCONH(CH_2)_3Si(OMe)_3$,

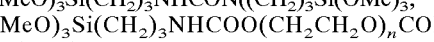

 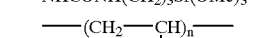

-continued

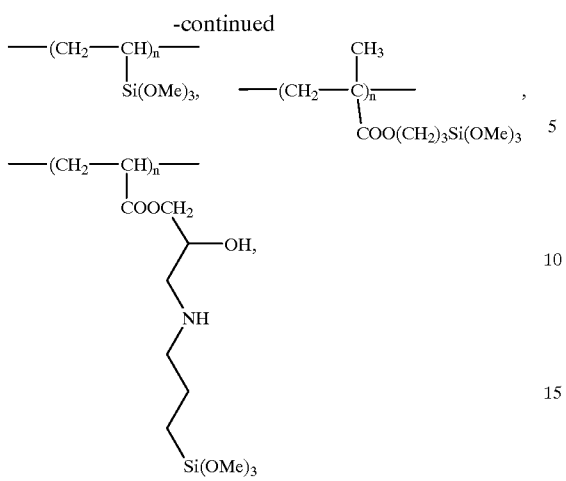

and combinations thereof where n = 1, 2, 3, or 4.

11. The composition of claim 8 further comprising a hydrophobic molecule.

12. A lipid vesicle composition comprising:
a plurality of silyl lipid molecules wherein said silyl lipid molecules further comprise at least one silanol group; wherein the at least one silanol groups of said plurality of silyl lipid molecules are joined together via siloxane bonds, further comprising a phospholipid.

13. A Langmuir lipid membrane composition comprising:
a plurality of silyl lipid molecules wherein said silyl lipid molecules further comprise at least one silanol group; wherein the silanol groups are joined together via siloxane bonds, further comprising phospholipid.

14. A lipid vesicle composition comprising cross-linked silyl lipid, said composition comprising siloxane bonds, further comprising a phospholipid.

15. The composition of claim 14, further comprising an inorganic-organic hybrid mixture sol-gel or uniform sol-gel bonded to said silyl lipid.

* * * * *

UNITED STATES PATENT AND TRADEMARK OFFICE
CERTIFICATE OF CORRECTION

PATENT NO.     : 6,284,163 B1
DATED          : September 4, 2001
INVENTOR(S)    : Sunney I. Chan, Michael H. B. Stowell and Guangyang Wang It is certified that error appears in the above-identified patent and that said Letters Patent is hereby corrected as shown below:

Column 1,
Line 4, please insert the following paragraph:

-- Statement of Government Rights

The U.S. Government may have certain rights in this invention pursuant to U. S. Government Grant No. GM22432 awarded by the National Institutes of Health. --

Signed and Sealed this

Twentieth Day of August, 2002

Attest:

JAMES E. ROGAN
*Attesting Officer*   *Director of the United States Patent and Trademark Office*